United States Patent [19]

Loosemore

[11] Patent Number: 4,817,442
[45] Date of Patent: Apr. 4, 1989

[54] SAMPLE SPLITTER

[75] Inventor: John C. Loosemore, Applecross, Australia

[73] Assignee: Brian Christoperh Coupe, Kingsley, Australia

[21] Appl. No.: 98,764

[22] PCT Filed: Nov. 1, 1985

[86] PCT No.: PCT/AU85/00268
§ 371 Date: Jun. 26, 1986
§ 102(e) Date: Jun. 26, 1986

[87] PCT Pub. No.: WO86/03001
PCT Pub. Date: May 22, 1986

Related U.S. Application Data

[63] Continuation of Ser. No. 887,099, Jun. 26, 1986, abandoned.

[51] Int. Cl.⁴ ............................................. G01N 1/12
[52] U.S. Cl. ................................................. 73/863.56
[58] Field of Search ........... 73/863.31, 863.41, 863.43, 73/863.45, 863.51, 863.56, 863.57, 863.61

[56] References Cited

U.S. PATENT DOCUMENTS

| 27,582 | 3/1860 | Gelder | 73/863.56 |
| 78,099 | 5/1868 | Keller | 73/863.41 |
| 888,471 | 5/1908 | Constant | 73/863.56 |
| 1,215,988 | 2/1917 | Pott | 73/863.56 |
| 2,405,951 | 8/1946 | Herrold | 73/863.61 |
| 3,380,306 | 4/1968 | Pazandak | 73/863.56 |
| 3,433,078 | 3/1969 | Thompson | 73/863.56 |

FOREIGN PATENT DOCUMENTS 0569894  8/1977  U.S.S.R. ............................ 73/863.56

Primary Examiner—Stewart J. Levy
Assistant Examiner—Robert R. Raevis
Attorney, Agent, or Firm—Harness, Dickey & Pierce

[57] ABSTRACT

A sample splitter comprising a housing having a substantially cylindrical rotor chamber having at least one inlet, at least two outlets, and a rotor rotatably received in the rotor chamber, said rotor being subdivided into at least two separate zones wherein each zone communicates with said inlet on rotation of the rotor, and each zone communicates with a different outlet from the other zone.

7 Claims, 5 Drawing Sheets

SAMPLE SPLITTER

CROSS REFERENCE TO RELATED APPLICATION

This is a continuation of U.S. patent application Ser. No. 887,099, filed June 26, 1987, now abandoned.

BACKGROUND OF THE INVENTION

This invention relates to a sample splitter for sampling from a quantity of material.

SUMMARY OF THE INVENTION

In one form the invention resides in a sample splitter comprising a housing having a substantially cylindrical rotor chamber having at least one inlet, at least two outlets and a rotor rotatably received in the rotor chamber, said rotor being sub-divided in to at least two separate zones wherein each zone communicates with said inlet on rotation of the rotor, and each zone communicates with a different outlet from the other zone.

According to a preferred feature of the invention, at least one of said outlets accommodates a barrier therein to define two flow paths.

According to a preferred feature of the previous feature, there are three outlets, two of which accommodate said barrier and wherein one flow path from at least one outlet delivers material to a separate sample collector.

According to a preferred feature of the invention the rotation axis of the rotor is substantially horizontal.

According to a preferred feature of the invention the inlet is located above the rotor.

According to a further preferred feature of the invention the outlet is located below the rotor.

According to a preferred feature of the invention the zones are located in axial side by side relationship.

According to a further preferred feature of the invention each zone is sub-divided into a set of pockets angularly disposed around the axis of rotation and wherein each of the pockets communicates with the inlet on rotation of the rotor.

BRIEF DESCRIPTION OF THE DRAWINGS

The invention will be more fully understood in the light of the following description of one specific embodiment. The description is made with reference to the accompanying drawings of which.

DETAILED DESCRIPTION OF THE PREFERRED EMBODIMENT

Figure 1:
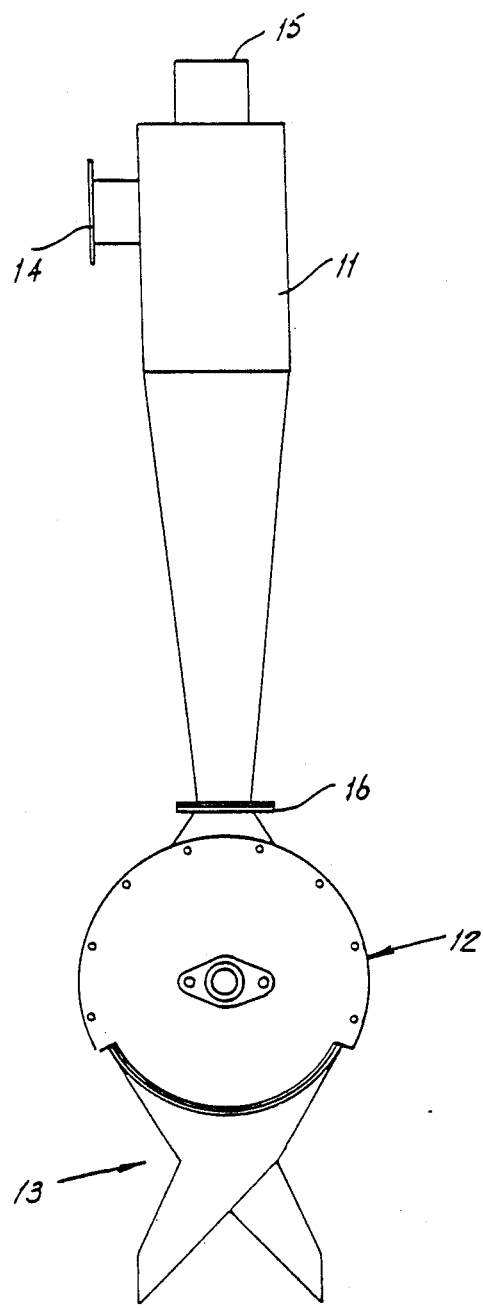
FIG. 1 is an elevational view of the sample splitter of the embodiment.

The embodiment is directed towards a sample splitter for splitting substantial quantities of fluid solid particulate material and/or slurries such as borehole cuttings. The sample splitter is connected to a cyclone 11 which has an inlet 14 located towards the top thereof which receives the flow of air and/or liquid and entrained particulate materials such as cuttings from a borehole. The top of the cyclone has an outlet 15 to permit air to escape. The cuttings fall to the bottom of the cyclone 11 and enter the sample splitter 12 at its inlet 16.

Figure 2:
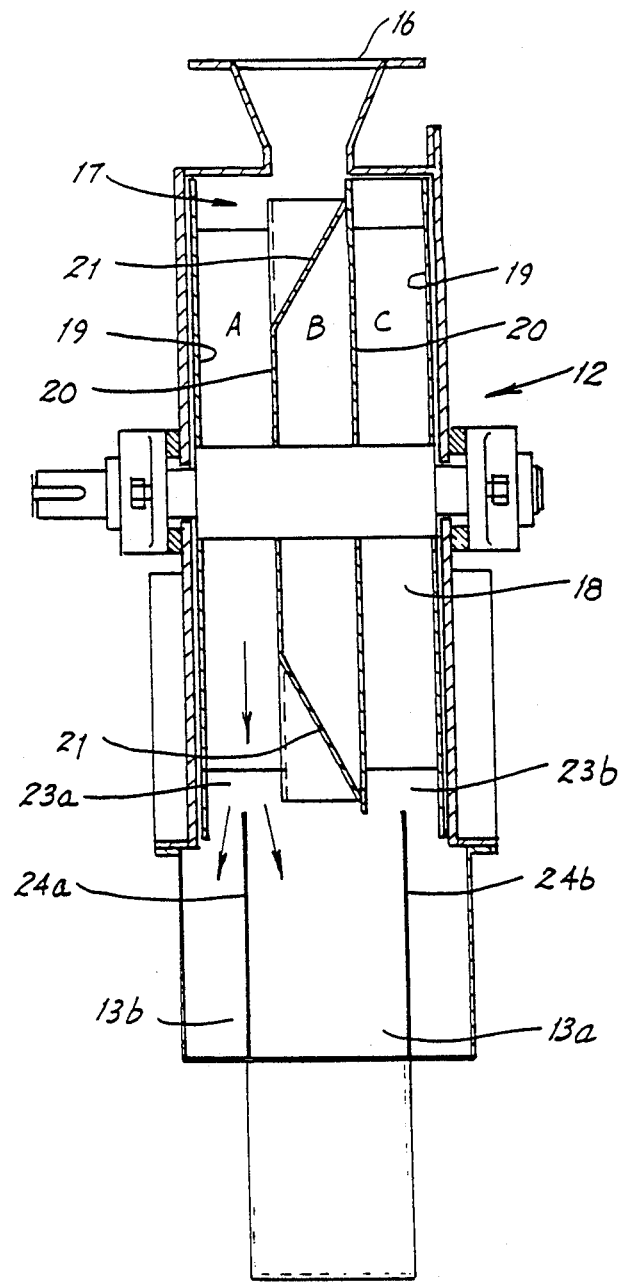
FIGS. 2, 3 and 4 are sectional elevations of the sample splitter in its three different sampling modes.
Figure 3:
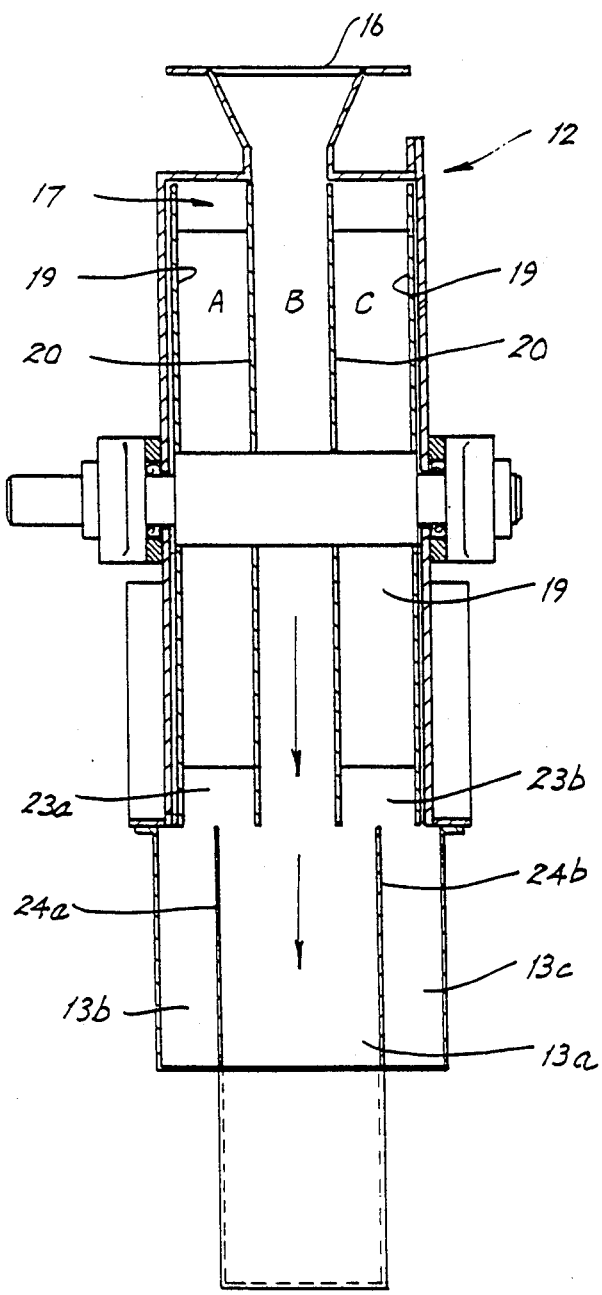
Figure 4:
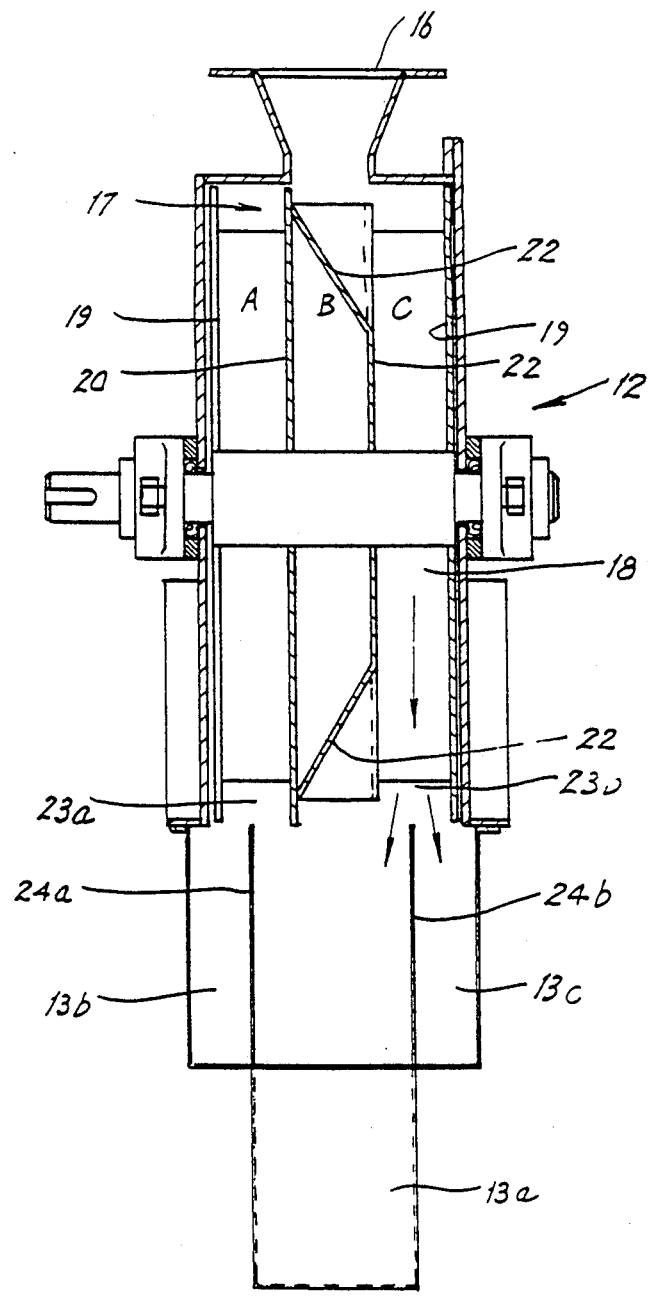

The sample splitter 12 comprises a substantially cylindrical rotor chamber 17 having its central axis substantially horizontal which accommodates a substantially cylindrical rotor 18 mounted for rotation about the central axis of the rotor chamber 17. The rotor is defined into three axially disposed annular zones A, B and C which are defined by means of two end plates 19 and two intermediate plates 20. The central zone B is divided into a plurality of radially disposed pockets by means of a set of equally spaced radial plates extending between the intermediate separator plates 20. One half of the pockets are defined by the radial plates and the intermediate separator plates 20 such that when the pockets are located below the inlet 16, material flowing into the splitter from the inlet 16 is deposited into the central zone B as shown at figure 3. An additioal one quarter of the pockets in the central zone B are formed with first oblique diverter plates 21 which close off the entry into the pocket and cause material flowing into the central zone B from the inlet 16 of the splitter to be diverted into one end zone A of the rotor as shown at FIG. 2. The remaining one quarter of the pockets in the central zone B of the rotor are formed with second obliquely located diverter plates 22 which are opposed to the first oblique diverter plates 21 and close off the pocket of the central zone B of the rotor and divert material flowing into central zone B from the inlet 16 of the splitter into the other end zone C located at the other side of the central zone B as shown at FIG. 4. Each of the end zones A and C are formed with pockets by means of radial plates which may if desired be located at corresponding positions to the radial plates forming the pockets in the central zone B.

In operation, as material is delivered to the sample splitter 12 from the cyclone 11 through the inlet 16, the rotor 18 is caused to rotate. As each of the open central pockets of the central zone B pass underneath the inlet 16, material is collected in the pockets of the central zone B and on further rotation of the rotor, this material is deposited into a centrally located outlet 13a. As each of the pockets of the one end zone A which communicates with the central zone B (see FIG. 2) pass beneath the inlet 16, material is collected in those pockets and on further rotation of the rotor, that material is deposited into a first outlet 23a at one side of the central outlet 13a. The first outlet 23a is divided into two flow paths, of substantially equal cross-sectional area by a centrally located barrier 24a. As a result one half of the material from the pocket is delivered to the central outlet 13a and the other half of the material from the pocket is delivered to a side chute 13b. Similarly, as the pockets of the other end zone C (see FIG. 4), which communicates with the central zone B of the rotor, pass below the inlet 16, material from the inlet 16 is diverted into the pockets of the other end zone C and on further rotation of the rotor, the material is delivered to a second outlet 23b on the other side of the central outlet 13a. The second outlet 23b is also divided into two flow paths of substantially equal cross-sectional area by a central located barrier 24b. As a result one half of the material from the pocket flows to the central outlet 13a and the other half of the material from a pocket flows to a second side chute 13c.

As a result of the embodiment, a sample splitter is produced which separates a quantity of material flowing into the splitter into two samples of approximately 12½% of the total material and a further sample which comprises approximately 75% of the material. If desired the samples collected may be split further by dividing the flow paths further.

The embodiment provides a sample splitter which by virtue of the rotor 18 provides an air lock valve to prevent any air escaping from the cyclone 11 and passing through the splitter to upset any of the sampling procedures. Particulate material moving under gravity within the splitter has minimal velocity and therefor has no opportunity to segregate according to particle size of density.

Figure 5:
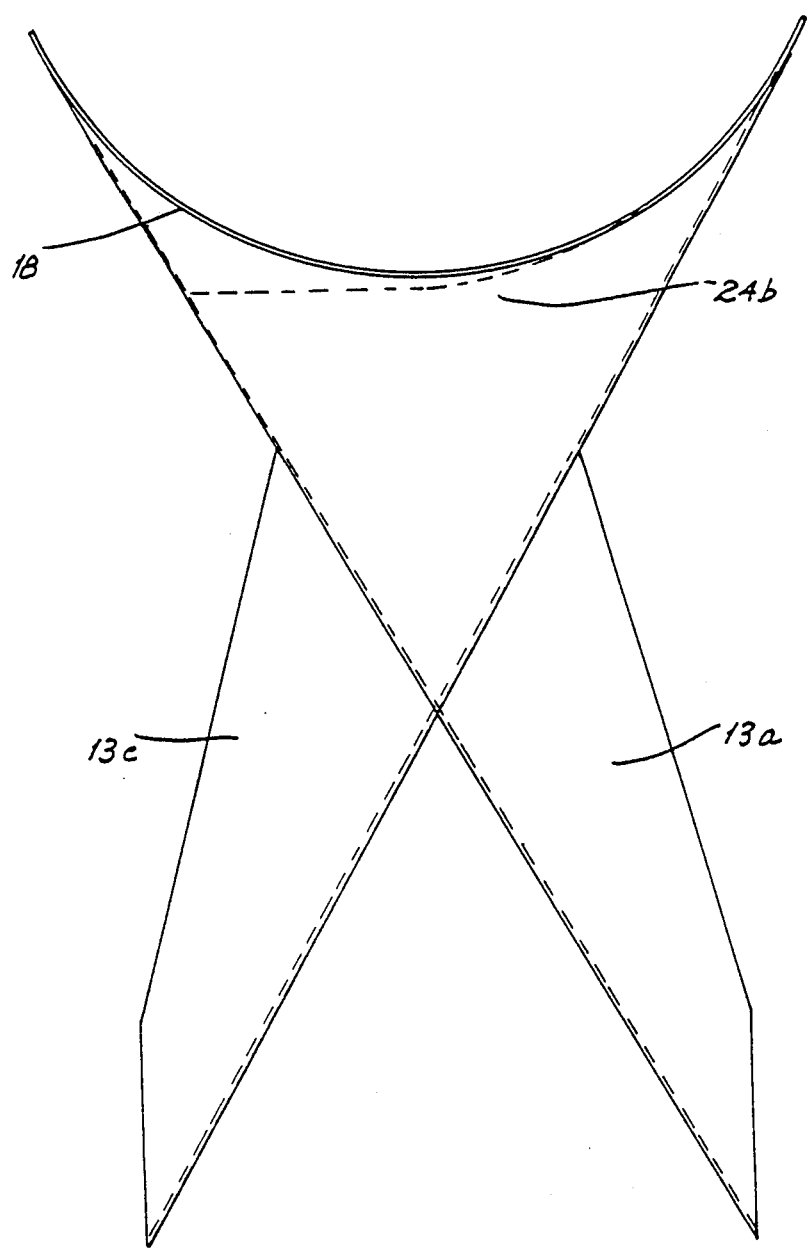
FIG. 5 is a part sectional view of the delivery chutes of the embodiment.

If desired, the barriers 24a and 24b at the outlets 23a and 23b of the two end zones A and C are shaped as shown at FIG. 5 such that their upper edge diverges away from the periphery of the rotor 18 with rotation of the rotor in order that any large particles which may be riding over the barriers do not become jammed between the barriers and the rotor. In addition if desired the unsplit material may be delivered to the rotor chamber through the end most zones A and C rather than the central zone.

If desired the zones need not be sub-divided into pockets and there may be a somewhat direct communication between the inlet and outlet. In such a case the rotor would not serve as a valve or air lock.

It should be appreciated that the scope of the present invention need not be limited to the particular scope of the embodiment described above. The invention may be used with any form of material which may be in a wet or dry form. In addition the material may be introduced into the splitter by any suitable means and need not be introduced direct from its source. Furthermore the relative volume of material delivered to each zone may vary as desired.

The claims defining the invention are as follows:

I claim:

1. A sample splitter comprising a housing having a substantially cylindrical rotor chamber defined by a cylindrical peripheral wall and a pair of generally planar end walls, at least one inlet to said rotor chamber formed in said peripheral wall, at least two outlets from said rotor chamber formed in said peripheral wall and circumferentially spaced from said inlet, and a cylindrical rotor rotatably received in the rotor chamber, said rotor being substantially complimentary in shape to said motor chamber and being sub-divided into at least two separate axially spaced zones, each of said zones being divided into pockets circumferentially spaced from each other for precluding samples from flowing directly from said inlet to any of said outlets without passing through at least one of said rotor pockets, each pocket communicating sequentially with said inlet on rotation of the rotor, and at least one of said pockets communicates with a different outlet from another of said pockets.

2. A sample splitter as claimed in claim 1 wherein one of said outlets is divided by a barrier to define two different flow paths.

3. A sample splitter as claimed in claim 2 wherein there are three outlets, at least two of said outlets each being divided by a respective barrier.

4. A sample collector as claimed in claim 1 wherein said pockets of each zone alternately communicate with the inlet.

5. A sample splitter as claimed at claim 1 wherein the rotation axis of said rotor is substantially horizontal.

6. A sample splitter as claimed at claim 5 wherein the outlets are located below the rotor.

7. A sample splitter as claimed at claim 5 wherein the one inlet is located above the rotor.

* * * * *